United States Patent [19]

Boudakian et al.

[11] Patent Number: 5,112,983

[45] Date of Patent: May 12, 1992

[54] PROCESS FOR PRODUCING 1,2,4-TRIAZOL-5-ONE USING ORGANIC SULFONIC ACIDS AND POLYMERS THEREOF AS A CATALYST

[75] Inventors: Max M. Boudakian, Pittsford; Delmer A. Fidler, Rochester, both of N.Y.

[73] Assignee: Olin Corporation, Cheshire, Conn.

[21] Appl. No.: 546,977

[22] Filed: Jul. 2, 1990

Related U.S. Application Data

[63] Continuation-in-part of Ser. No. 101,465, Sep. 28, 1987, Pat. No. 4,999,434.

[51] Int. Cl.$^5$ .......................................... C07D 249/12
[52] U.S. Cl. .................................................. 548/263.2
[58] Field of Search ...................................... 548/263.2

[56] References Cited

U.S. PATENT DOCUMENTS

| | | | |
|---|---|---|---|
| 2,763,661 | 9/1956 | Grundmann et al. | 260/308 |
| 3,041,317 | 6/1962 | Gibbs et al. | 260/79.3 |
| 3,282,875 | 11/1966 | Connolly et al. | 260/29.6 |
| 3,560,568 | 2/1971 | Resnick | 260/513 |
| 3,718,627 | 2/1973 | Grott | 260/79.3 |
| 4,467,098 | 8/1984 | Koch et al. | 548/263.2 |
| 4,482,739 | 11/1984 | Rothgery | 564/37 |
| 4,927,940 | 5/1990 | Boudakian et al. | 548/263.2 |

FOREIGN PATENT DOCUMENTS

| | | |
|---|---|---|
| 0210881 | 2/1987 | European Pat. Off. |
| 3114314 | 10/1982 | Fed. Rep. of Germany |
| 3114349 | 1/1983 | Fed. Rep. of Germany |

OTHER PUBLICATIONS

C. Runti et al. Chem. Abstracts 54; 22601-2, *Ann. Chim.* (Rome) 49, 1649-67 (1959), "Reactions Between Organic Nitrogen Compounds and Ethyl Orthoformates I. Hydrazides and Derivatives".

*Chemische Berichte*, vol. 98-II, "Synthesen and Reaktionen von 4-Amino-1.2.4-Triazolonen-(5)", pp. 3025-3033, 1965 C. F. Kroger et al.

*Chemische Berichte*, vol. 98-II, "Die Umsetzung Alkyl-substituierter Semicarbazide Mit Orthoameisensaure--triathylester" pp. 3034-3039, 1965.

H. Gehlen et al. Chem. Abstract, 62; 14437: *Ann Chem. 682*, pp. 123-135 (1965) "1.2.4-Triazol-5-ones, V. Effect of Substituents on the Rate of Hydrolysis in Half-Concentrated Sulfuric Acid".

G. Chipen et al. *Khim. Geterotsikl. Soedin., Akad. Nauk Latv. SSR*, 1966 (1) pp. 110-116 (Translated) "5-1,2,4--Triazolin-3-one and Its Nitro and Amino Derivatives".

*Chemische Berichte*, vol. 100-II, "Die Bromierung von 1,2,4-Triazolen", pp. 2250-2257 (1967).

Dobosz. Chem. Abst. 100; 34468: Univ. Mariae Curie-Sklodowska, Sect. AA: Chem 1 (Publ. 1982), 34, pp. 163-168 (Polish), "Triformylaminomethane. III. Reaction With Thiosemicarbazide, Semicarbazide and Aminoguanidine".

*Chemical Reviews*, "Formylating Agents", (G. A. Olah et al) *American Chemical Society*, vol. 87, No. 4, Aug. 1987, pp. 671-686.

Pennwalt Corp. Phila. Pa. No. S-107B "Methane Sulfonic Acid (MSA), Properties Reactions and Applications, publication", pp. 1-11.

*Primary Examiner*—Patricia L. Morris
*Attorney, Agent, or Firm*—Allen A. Meyer, Jr.; Paul Weinstein

[57] ABSTRACT

A process for producing 1,2,4-triazol-5-one reacts a semicarbazide compound with a formic acid compound in the presence of a catalytic amount of a catalyst. The catalyst is selected from the group consisting of an organic sulfonic acid and a sulfonic acid-containing polymer or co-polymer, and mixtures thereof. The novel process of the present invention produces 1,2,4-triazol-5-one having significantly lower concentrations of chloride ion which are advantageous, for example, in the production of 3-nitro-1,2,4-triazol-5-one as an explosive used in castable explosive compositions. The organic sulfonic acid compound catalyst can be recovered and reused.

20 Claims, No Drawings

PROCESS FOR PRODUCING
1,2,4-TRIAZOL-5-ONE USING ORGANIC
SULFONIC ACIDS AND POLYMERS THEREOF AS
A CATALYST

This application is a continuation-in-part application of U.S. Ser. No. 07/101,465 filed on Sept. 28, 1987, now U.S. Pat. No. 4,999,434.

BACKGROUND OF THE INVENTION

This invention relates to a process for the production of triazolone compounds. More particularly, the invention relates to a process for the production of 1,2,4-triazol-5-one from semicarbazide compounds.

1,2,4-Triazol-5-one (or its tautomeric form; 5-hydroxy-1H-1,2,4-triazole) is a known compound useful as an intermediate in the production of explosives and in the synthesis of dyestuffs.

The preparation of 1,2,4-triazol-5-one has been reported by a number of investigators. C. Runti et al [Ann. Chim. (Rome) 49, 1649–1667, 1959: Chem. Abstracts 54,22602k (1960)] refluxed semicarbazide.HCl with ethyl orthoformate for one hour, the reaction mixture cooled, filtered, and crystallized from ethanol to give 1,2,4-triazol-5-one.

C. F. Kroeger et al prepared 4-amino-1,2,4-triazol-5-one by heating carbohydrazide and ethylorthoformate on a water bath. The amino derivative was deaminated by treatment with $NaNO_2$ in HCl and neutralized with NaOH [Chem. Ber. 98 (9) 3025–3033 (1965); Chem. Abstracts 63,16339g (1965)].

1,2,4-Triazol-5-one was prepared by G. I. Chipen et al by several methods including the reaction of formic acid with acetone semicarbazone and with semicarbazide.HCl, the latter method being considered optimal. Semicarbazide.HCl and 85 percent formic acid were boiled for 8 hours and kept for 12 hours at 0°C. to prepare of 1,2,4-triazol-5-one. [Khim. Geterotsikl. Soed: 2 (1) 110–116 (1966); Chem. Abstracts 65,705b (1966)].

M. Dobosz prepared 1,2,4-triazol-5-one by the reaction of triformylaminomethane with semicarbazide or its hydrochloride as reported in Ann. Univ. Mariae Curie-Sklodowska, Sect. AA: Chem. 34, 163 (1979), Chem. Abstracts 100, 34468, (1984).

The preparations recorded in the prior art give 1,2,4-triazol-5-one in low yields or where semicarbazide.HCl is a reactant, the product contains high concentrations of chloride ions. In an important application, the triazolone compound is nitrated to produce 3-nitro-1,2,4-triazol-5-one which is used in cast explosive compositions. It is known that the presence of high chloride concentrations in castable explosives stored, for example, in metal casings results in increased corrosion of the casings and increased gas formation.

In addition, 1,2,4-triazol-5-one having high concentrations of chloride ion can undergo undesired chemical reactions. For example, Kroeger et al (op. cit.) found that when 3-nitro-1,2,4-triazol-5-one was heated with hydrochloric acid, chloro-denitration resulted and 3-chloro-1,2,4-triazol-5-one was formed in 87 percent yield.

Therefore, there is a need for a process for producing 1,2,4-triazol-5-one having reduced concentrations of impurities such as chlorides.

SUMMARY OF THE INVENTION

It is an object of the invention to provide a process for producing 1,2,4-triazol-5-one having lower amounts of impurities such as chlorides.

Another object of the invention is to provide a process for producing 1,2,4-triazol-5-one which is suitable for producing castable explosives having reduced concentrations of impurities.

These and other objects of the invention are accomplished in a process for producing 1,2,4-triazol-5-one by reacting a semicarbazide compound with a formic acid compound in the presence of a catalytic amount of an organic sulfonic acid and polymers thereof.

DETAILED DESCRIPTION OF THE INVENTION

The novel process of the present invention employs as one reactant a semicarbazide compound. Suitable semicarbazide compounds include semicarbazide, carbohydrazide, and salts thereof, with semicarbazide being preferred.

In the novel process of the present invention, the semicarbazide compound is reacted with a formic acid compound which results in the ring-forming or cyclization reaction required to produce the 1,2,4-triazol-5-one. Suitable formic acid compounds include formic acid, formic acid esters ($O_2R''$) or orthoformic acid esters ($OR''$)$_3$ having 1 to about 6 carbon atoms, alkali metal formates such as sodium formate or potassium formate, formamide, and triformylaminomethane.

Preferred as formic acid compounds are formic acid, and formic acid esters ($O_2R''$) or orthoformic acid esters ($OR''$)$_3$ having from 1 to about 3 carbon atoms. Examples of these preferred embodiments include methyl orthoformate, and ethyl orthoformate.

The novel process of the present invention employs catalytic amounts of an organic sulfonic acid or polymer thereof including alkyl sulfonic acids in which the alkyl group contains from 1 to about 6 carbon atoms and alkali metal salts thereof, fluoro substituted alkyl sulfonic acids in which the alkyl group contains from 1 to about 6 carbon atoms, alkyl disulfonic acids in which the alkyl group contains from 2 to about 6 carbon atoms and alkali metal salts thereof, and fluoro substituted alkyl disulfonic acids in which the alkyl group contains from 2 to about 6 carbon atoms. Organic sulfonic acid polymers include polymers and co-polymers as exemplified by ion exchange resins as well as alkyl and aromatic perfluorosulfonic acid resins.

Suitable alkyl sulfonic acids are exemplified by methanesulfonic acid, trifluoromethanesulfonic acid, ethanesulfonic acid, 1,2-ethanedisulfonic acid, 1,2-perfluoroethanedisulfonic acid, perfluorooctane sulfonic acid, and pentanesulfonic acid, sodium salt.

Polymers and co-polymers of organic sulfonic acid which may be employed as a catalyst in the process of the invention include sulfonated copolymers of styrene and divinylbenzene which are exemplified by the ion exchange resins Dowex® 50W-X8 (Dow Chemical Co.), Amberlyst® 15, Amberlyst® 31, Amberlyst® 36 (Rohm and Haas Co.), among others. In addition, sulfonated polymers such as poly(vinyl sulfonic acid) as well as co-polymers of vinyl sulfonic acid with vinyl alcohol or acrylic acid. Further, perfluorosulfonic acid polymers and co-polymers including resins such as those produced commercially and sold under the trademarks "NAFION" by E. I. Du Pont de Nemours &

Company, or "FLEMION" by Asahi Glass Company as well as aromatic perfluorosulfonic ion exchange resins produced by the sulfonation of polymerized polystyrene which have been developed by the General Electric Co., may be used.

The novel process of the present invention employs catalytic amounts of the organic sulfonic acids and polymers thereof which are, for example, admixed with the semicarbazide compound and the formic acid compound which enhance the production of 1,2,4-triazol-5-one. Suitable amounts include those, for example, which provide molar ratios of from about 0.05:1 to about 1:1, and preferably from about 0.1:1 to about 0.5:1. To conduct the process of the invention, the semicarbazide compound, the formylating agent and the catalyst are heated at temperatures up to about reflux to produce a reaction mixture containing 1,2,4-triazol-5-one. While the reaction is preferably conducted at about atmospheric pressure, superatmospheric pressures may be employed if desired. The reaction mixture is cooled and the product isolated by known procedures. Where formic acid is the formic acid compound, an azeotrope with water is formed which is stripped from the reaction mixture before cooling and recovering the 1,2,4-triazol-5-one product. Alternatively, the reaction product can be filtered and the filter cake washed with water.

When semicarbazide (i.e., semicarbazide as a free base) is reacted with a formic acid ester in the presence of the catalytic amount of organic sulfonic acid or polymers thereof by the process of the invention, 1,2,4-triazol-5-one is produced as the sole product. This is significant in view of the known reaction of semicarbazide with a formic acid ester where, in the absence of the organic sulfonic acid or polymers as catalyst, hydrazodicarbonamide is produced as reported by C. Kroeger et al in Chem. Ber. 98, 3034 (1965).

In an alternate embodiment of the process of the invention, The semicarbazide compound and the formic acid compound are continuously passed through a preheated bed of the sulfonic acid-containing polymer catalyst. The reaction mixture produced is then distilled to separate the formic acid compound and the 1,2,4-triazol-5-one product recovered.

The semicarbazide compound employed in the reaction may itself be produced in situ from a hydrazine compound. For example, semicarbazide may be produced by reacting aqueous hydrazine with urea to form a reaction mixture of semicarbazide and ammonia, concentrating the reaction mixture, admixing a formic acid compound into the reaction mixture, and heating the reaction mixture to produce 1,2,4-triazol-5-one.

The use of carbohydrazide as the semicarbazide compound produces an amino-substituted 1,2,4-triazol-5-one which is deaminated by known procedures to provide the desired product.

The novel process of the present invention produces 1,2,4-triazol-5-one having significantly lower concentrations of chloride ion which are advantageous, for example, in the production of 3-nitro-1,2,4-triazol-5-one as an explosive used in castable explosive compositions. The organic sulfonic acid compound catalyst can be recovered and reused, perhaps after regeneration.

The following examples further illustrate the novel process of the invention without any intention of being limited thereby. All parts and percentages are by weight unless otherwise specified.

EXAMPLE 1

1,2,4-Triazol-5-One from Aqueous Semicarbazide-free Base/formic Acid/methanesulfonic Acid

1. 'Virgin' Conditions

To aqueous semicarbazide-free base (59.2% concentration; 126.8 g.;1.0 mole) was added 90% formic acid (127.9 g.; 2.5 moles), followed by 70% aqueous methanesulfonic acid (137.2 g.; 1.0 mole). The reactants were heated at 109° C. for 5.25 hours. Unreacted formic acid ($H_2O$ azeotrope) was distilled (130 ml.) Water (100 ml.) was added to remove residual formic acid as the $H_2O$-azeotrope (110 ml.). The crude product was recrystallized from $H_2O$ (75ml.; 90° C.), cooled to 0–10° C. and the supernatant liquid siphoned. A second recrystallization was performed with additional water (75 ml.; 90° C.), cooled to 0–10° C. and the supernatant liquid siphoned. The weight of combined supernatant liquors was 280 g. (retained for recycle). The white cake was transferred with $H_2O$(75 ml.) and vacuum-dried to give product, (50.7 g.; 0.596 mole; 59.6% yield) having a m.p. 235-36° C. which was identified as 1,2,4-triazol-5-one (HPLC) assay was 99.2%. Anal.: $Cl^-$,0.012%;Fe, 0.9 ppm; S, 0.7%. The aqueous wash liquor (wt. 134.5 g) was retained for recycle.

EXAMPLE 2

2. Recycle of Process Liquors

OBJECTIVE: The process liquors from the previous example containing methanesulfonic acid and solubilized 1,2,4-triazol-5-one were recycled without need of further catalyst addition.

Combined supernatant (wt. 280 g.) and aqueous wash (wt. 134.5 g.) liquors were concentrated (250 ml. $H_2O$ removed) and aqueous semicarbazide free base (59.2% conc'n; 126.8 g.; 1.0 mole) added at 13 to 30° C. 90% Formic acid (127.9 g.; 2.5 moles) was then added and the reactants heated at 112° C. for 5.25 hours. Unreacted formic acid ($H_2O$ azeotrope) was distilled (130 ml). Water (100 ml.) was added to remove residual formic acid as the $H_2O$-azeotrope (130 ml). The crude product was crystallized from $H_2O$ (75 ml.; 90° C.), cooled to 0–10° C. and the supernatant liquid siphoned. A second recrystallization was performed with additional water (75 ml.; 90° C.), cooled to 0–10° C. and the supernatant liquid siphoned. The white cake was transferred with $H_2O$(75 ml.) and vacuum-dried to give a product, m.p. 235-37° C. (64.1 g.; 0.753 mole; 75.3% yield). 1,2,4-Triazol-5-one (HPLC) assay was 99.0%. Anal.: $Cl^-$,0.01%; Fe, 1.93 ppm; S, 0.55%.

EXAMPLE 3

1,2,4-Triazol-5-One: From Aqueous Semicarbazide Free Base/formic Acid and Cross-linked Polystyrene Sulfonic Acid (H+Ionic Form)

1. Amberlyst TM 15 Ion Exchance Resin

OBJECTIVE: This Example demonstrated that cross-linked polystyrene sulfonic acids could serve as cyclization catalysts A mixture consisting of aqueous semicarbazide free base (42.4% concentration; 423.0 g.; 2.39 moles), 90% formic acid (305.6 g.; 6.0 moles) and Amberlyst TM 15 ion exchange resin (Polysciences. Cat. No. 8356;<3% $H_2O$; 4.7 meq./gm. ion exchange capacity) was heated at 106° C. for 5 hours. Unreacted formic acid ($H_2O$ azeotrope) was distilled (150 ml.). Water (200 ml.) was added to remove residual formic acid as the H$_2$O-azeotrope (325 ml.). The product was H$_2$O-extracted from the Amberlyst TM 15 ion exchange resin (recovered catalyst, 583 g., wet). The filtrate, wt. 1308 (g), was treated with Darco KB charcoal (9.0 g.), and concentrated (1,000 ml. distilled) and cooled to 10° C. The mother liquor was siphoned (77.6 g.) and the white cake was transferred by H$_2$O (50 ml.). The dried (50° C./10 mm.) crude product melted at 180-205° C. (66.9 g.; 0.787 mole; 32% yield). The crude product was recrystallized from H$_2$O (155 ml.; 90-95° C.), cooled to 10° C. and the supernatant liquid siphoned (96.5 g.). The recrystallized product was transferred with H$_2$O (50 ml) and dried, m.p. 214-21° C. (41.0 g.; 0.482 mole; 26.2% yield). A second recrystallization was perfomed with additional water (96 ml.; 90-95° C., cooled to 10° C. and the supernatant liquid siphoned. The white cake was transferred with H$_2$O (50 ml.) and dried to give product, m.p. 233-36° C. (26.2 g.; 0.308 mole; 12.9% yield). The 1,2,4-triazol-5-one assay (HPLC) was 96.1%. Chloride and iron content was 0.029 wt. % and 10.2 ppm, respectively.

EXAMPLE 4

A. AMBERLYST ® 15 ion Exchange Resin (wet type)

Objective: To asess efficacy of the wet form of Amberlyst ® 15 Ion Exchange Resin.

A mixture consisting of semicarbazide free base (54.4% concentration; 138.0 g.; 1.0 mole) 90% formic acid (127.9 g.; 2.5 moles) and Amberlyst ®15 ion exchange resin (wet type; Aldrich Cat. No. 21,639-9; wt. 212.8 g.; ion exchange capacity, 4.7 meq./gm) was heated at 104° C. for 11 hours. Unreacted formic acid (H$_2$O azeotrope was distilled [170 ml]). Water (125 ml) was added to distill residual formic acid (130 ml).

The cooled (25° C.) reaction mixture was diluted with H$_2$O (400 ml), Darco KB charcoal (7 g.) added and the reactants filtered through diatomaceous earth. The filtrate was concentrated and the cooled (0° C.) reaction mixture filtered. The vacuum-dried (50° C./10 mm) non-recrystallized product, wt. 14.44 g. (0.17 mole; 17% yield) melted at 218-223° C. and assayed 70.5% 1,2,4-triazol-5-one by HPLC.

EXAMPLE 5

2. Fresh Amberlyst TM 31 Ion Exchange Resin

A mixture consisting of aqueous semicarbazide free base (63.2% concentration; 118.8 g.; 1.0 mole), 88% formic acid (130.8 g.; 2.5 moles) and Amberlyst TM 31 ion exchange resin (wt. 360.7 g.; 60-66% H$_2$O; 1.4 meq./gm. ion exchange capacity) was heated at 103° C. (22.5 hrs.).

The product was extracted with H$_2$O (2 liters) from Amberlyst TM 31 ion exchange resin (wt. recovered catalyst, 330 g.).

The aqueous extract was concentrated (1350 ml. distilled), and residual solids recrystallized from H$_2$O (75 ml.; 90-5° C.). The supernatant liquid was siphoned and recrystallization was again performed with H$_2$O (75 ml.). The combined recrystallization liquors (wt. 118.0 g.) were retained for recycle. Double-recrystallized product was transferred with H$_2$O (75 ml./0° C.) and vacuum-dried, m.p. 236-39° C. (wt. 40.0 g.; 0.471 mole; 47.1% yield). 1,2,4-Triazol-5-one assay was 98.7% (HPLC) and contained negligble chloride (0.03%) and iron (6.2 ppm). The aqueous wash (wt. 173 g.) from the final triazolone transfer was retained for recycle.

EXAMPLE 6

Recycle Amberlyst TM 31 Exchange Resin

OBJECTIVE: To establish feasibility of concept of recycling recovered ion exchange catalyst and recycle of processing liquors from a virgin run.

A mixture consisting of semicarbazide -free base (63.2% conc'n; 72.7 g.; 0.61 mole), 88% formic acid (80.0 g.; 1.53 moles) and recovered wet Amberlyst TM 31 ion exchange resin (220.8 g.) was heated at 103° C. (23.8 hrs). The recovered catalyst was used as recovered and not acidified prior to recycle. Unreacted aqueous formic acid (67 ml.) was distilled. Further stripping was performed by addition of combined recrystallization and aqueous transfer liquids (wt. 180.4 g.) from Example 5 to give 175 ml. of distillate. The product was extracted with H$_2$O (2 liters). The weight of recovered wet Amberlyst TM 31 catalyst was 231.7 g.

The filtrate was concentrated (2050 ml. distilled) and the cooled (10° C.) mother liquor siphoned (58.5 g.). The residual solids were recrystallized from H$_2$O (50 ml.; 90-5° C.), the supernatant liquid (67 ml.) siphoned, followed by product transfer with H$_2$O (50 ml.) and vacuum-drying. The product melted at 220-22° C., wt. 17.9 g.; 0.210 mole; 34.4% yield).

Further recrystallization from H$_2$O (60 ml.; 90-5° C.) gave 10.79 g. 1,2,4-triazol-5-one (0.127 mole; 20.8% yield), m.p. 230-4° C. Product purity was 92.4% (HPLC) with low chloride (0.06%) and iron (6.0 ppm).

EXAMPLE 7

B. AMBERLYST ® 36 Ion Exchange Resin

Objective: To demonstrate the efficacy of another embodiment of cross-linked polystyrene sulfonic acid catalyst A mixture consisting of aqueous semicarbazide free base (59.2% concentration; 12.8 g.; 1.0 mole), 90% formic acid (127.9 g.; 2.5 moles) and Amberlyst ®36 ion exchange resin (Rohm & Haas Co., alternate designation: Amberlyst ®386; wt. 384.6 g.; H$_2$O, 40-60%; ion exchange capacity, 5.2 meq./g.) was heated at 103° C. (11.25 hrs.). The mother liquor (0-10° C.) was siphoned and the product extracted with H$_2$O (1750 ml) from the heterogeneous mixture (wt. of recovered wet catalyst, 378.0 g.).

The extract was concentrated (1,900 ml stripped), cooled to 10° C., then washed with H$_2$O (50 ml/0° C.) and filtered. Vacuum-dried non-crystallized 1,2,4-triazol-5-one weighed 44.05 g. (0.518 mole; 51.8% yield); m.p. 238–41° C.; and, assayed 96.9% (HPLC). Chloride and iron content was 0.039% and 4.9 ppm, respectively.

EXAMPLE 8

C. DOWEX ®50W-X8 Ion Exchange Resin

Objective: To evaluate an additional embodiment of a strongly acidic, cation exchange cross-linked, polystyrene sulfonic acid resin catalyst A mixture consisting of aqueous semicarbazide free base (54.4% concentration; 138.0 g.; 1.0 mole), 90% formic acid (127.9 g.; 2.5 moles) and DOWEX ®50W-X8, H+(J. T. Baker Cat. No. 1-1927; 20-50 mesh; 107 gms.; 51% moisture; exchange capacity, 4.83 meq./gm) was heated at 104° C. for 10.25 hrs. Unreacted formic acid was distilled as the H$_2$O azeotrope (155 ml). H$_2$O (125 ml) was added to distill residual formic acid (126 ml).

H$_2$O (300 ml) was added to the reaction mixture, the resin filtered and washed with additional H$_2$O (100 ml). The filtrate was concentrated, cooled to 10° C. and the mother liquor (110.7 gms.) siphoned. The residual solid was treated with H$_2$O (100 ml/0° C.), filtered and vacuum-dried (50° C./10 mm). Crude 1,2,4-triazol-5-one product weighed 15.0 g. (0.176 mole; 17.6% yield), melted at 232–4° C. and assayed 90.7% (HPLC).

EXAMPLE 9

D. Perfluorosulphonic Acid Resins (NAFION ®) (Expt. F63156)

A mixture consisting of semicarbazide free base (m.p. 91–4° C.; 75.07 g.; 1.0 mole), 90% formic acid (127.9 g.; 2.5 moles) and perfluorinated ion exchange powder (Aldrich No. 27,469-0; hydrogen ion form; equivalent weight, 1,100. Prepared from NAFION ® 117 perfluorinated membrane; 5.0 grams) was heated at 103–120° C.(4 hours). Unreacted formic acid was distilled as the H$_2$O azeotrope (52 ml). Water (40 ml) was added to distill residual formic acid (117 ml).

The cooled (25° C.) mixture was treated with water (200 ml) and the resin filtered (wt. of dried recovered catalyst, 5.88 gms). The filtrate was concentrated, the residual fluid cooled, the white precipitate filtered and vacuum-dried. Crude 1,2,4-triazol-5-one, wt. 7.89 gms. (0.093 mole; 9.3% yield), had m.p. 175–200° C.

sisting of perfluorosulfonic acid resins, sulfonated copolymers of styrene and divinylbenzene, poly(vinyl sulfonic acid), co-polymers of vinyl sulfonic acid and mixtures thereof to produce a reaction mixture containing 1,2,4-triazol-5-one.

2. The process of claim 1 in which the catalytic amount of the catalyst is a molar ratio to the semicarbazide compound of from about 0.05:1 to about 1:1.

3. The process of claim 1 in which the semicarbazide compound is semicarbazide or carbohydrazide, and salts thereof.

4. The process of claim 3 in which the molar ratio of the catalyst to the semicarbazide compound is from about 0.1:1 to about 0.5:1.

5. The process of claim 4 in which the formic acid compound is selected from the group consisting of formic acid, formic acid esters of an alcohol having 1 to about 6 carbon atoms, orthoformic acid esters of an alcohol having 1 to about 6 carbon atoms, alkali metal formates, formamide, and triformylaminomethane.

6. The process of claim 5 in which the semicarbazide compound is semicarbazide.

7. The process of claim 6 in which the sulfonic acid containing-polymer is an alkyl perfluorosulfonic acid resin or an aromatic perfluorosulfonic acid resin.

8. The process of claim 6 in which the sulfonic acid containing-polymer is a co-polymer of styrene and divinylbenzene.

9. The process of claim 6 in which the sulfonic acid

TABLE I

| | | | | | | | TRIAZOLONE | | | | |
|---|---|---|---|---|---|---|---|---|---|---|---|
| | | 70% CH$_3$SO$_3$H | HCO$_2$H | Aq. SC-Free Base | Reflux Time | # | % | M.P. | HPLC | Fe | Cl$^-$ |
| Example | System | Moles | Moles | (Moles)(a) | (hrs) | Rex'ins | Yield | (°C.) | (%) | (ppm) | (%) | (%) |
| 1 | Virgin | 1.0 | 2.5 | 1.0 | 5.25 | 2 | 59.6 | 235–236 | 99.2 | 0.9 | 0.0117 | 0.7 |
| 2 | 1st Recycle | 0 | 2.5 | 1.0 | 5.25 | 2 | 75.3 | 235–237 | 99.0 | 1.93 | 0.01 | 0.55 |

TABLE II 1,2,4-TRIAZOL-5-ONE VIA CROSS-LINKED POLYSTYRENE SULFONIC ACID CYCLIZATION CATALYSTS

| Example Number: | Description Trade Name. | Wt. (g.) | SC-Free Base Moles | HOC$_2$H (Moles) | % Yield | 1,2,4-Triazol-5-one Product HPLC Assay | M.P. (°C.) | % Cl– | Fe(ppm) |
|---|---|---|---|---|---|---|---|---|---|
| 3 | Amberlyst TM 15 (Dry) | 213 | 2.4 | 6.0 | 12.9$^a$ | 96.1 | 233–36 | 0.029 | (—) |
| 4 | Amberlyst TM 15 (Wet) | 213 | 1.0 | 2.5 | 17.0$^b$ | 70.5 | 218–23 | (—) | (—) |
| 5 | Amberlyst TM 31 (Wet) | 361 | 1.0 | 2.5 | 47.1$^c$ | 98.7 | 236–39 | 0.03 | 6.2 |
| 6 | Amberlyst TM 31 (Wet) | 221$^d$ | 0.6 | 1.5 | 20.8$^c$ | 92.4 | | | |
| 7 | Amberlyst TM 36 (Wet) | 385 | 1.0 | 2.5 | 51.8$^b$ | 96.9 | 238–42 | 0.04 | 4.9 |
| 8 | Dowex TM 50W-X8 (wet) | 107 | 1.0 | 2.5 | 17.6$^b$ | 90.7 | 232–34 | (—) | (—) |

NOTE:
$^a$Double-recrystallized product. Yield of crude product: 32.9%
$^b$Crude product recrystallization).
$^c$Double-recrystallized product
$^d$Catalyst recycled, not acidified.

TABLE III 1,2,4-TRIAZOLONE VIA POLY(PERFLUOROSULFONIC ACID) RESIN CATALYSTS

| Example Number: | Perfluorosulfonic Acid Resin Name: | Wt. (g.) | SC-Free Base (Moles) | HCO$_2$H (Moles) | % Yield | HPLC Assay | Triazolone Product M.P. (°C.) |
|---|---|---|---|---|---|---|---|
| 9 | NAFION TM 117 | 5$^a$ | 1.0 | 2.5 | 9.3 | (—) | 175–200 |

NOTE: $^a$Perfluorinated ion exchange powder (hydrogen ion form) Equiv. Wt. 1,100 (Aldrich 27,469-0)

What is claimed is:

1. A process for producing 1,2,4-triazol-5-one which comprises reacting a semicarbazide compound with a formic acid compound in the presence of a catalytic amount of a sulfonic acid catalyst selected from the group consisting of alkyl sulfonic acids and a sulfonic acid-containing polymer selected from the group concontaining-polymer is a poly(vinyl sulfonic acid).

10. The process of claim 6 in which the sulfonic acid containing-polymer is a co-polymer of vinyl sulfonic acid and vinyl alcohol or acrylic acid.

11. The process of claim 3 in which the semicarbazide compound is carbohydrazide.

12. The process of claim 5 in which the formic acid compound is a formic acid ester of an alcohol having 1 to 3 carbon atoms.

13. The process of claim 5 in which the formic acid compound is an orthoformic acid ester of an alcohol having 1 to 3 carbon atoms.

14. The process of claim 8 in which the sulfonic acid containing-polymer is an ion exchange resin in the hydrogen form.

15. The process of claim 1 in which the reaction mixture is distilled to separate the formic acid compound from a first mother liquor.

16. The process of claim 15 in which crystals of 1,2,4-triazol-5-one are precipitated from the first mother liquor.

17. The process of claim 16 in which the crystals of 1,2,4-triazol-5-one are recrystallized in an aqueous solution and separated from a second mother liquor.

18. A process for producing 1,2,4-triazol-5-one which comprises passing a semicarbazide compound and a formic acid compound through a heated bed of a sulfonic acid-containing polymer or co-polymer catalyst to produce a reaction mixture containing 1,2,4-triazol-5-one.

19. The process of claim 18 in which the catalyst is a sulfonated copolymer of styrene and divinylbenzene.

20. The process of claim 1 in which the alkyl sulfonic acids are alkyl monosulfonic acids, fluoro substituted alkyl monosulfonic acids, alkyl disulfonic acids and fluoro substituted alkyl disulfonic acids in which the alkyl group contains from 1 to about 6 carbon atoms, and alkali metal salts thereof.

* * * * *